US009750777B2

(12) United States Patent
Matheson et al.

(10) Patent No.: US 9,750,777 B2
(45) Date of Patent: Sep. 5, 2017

(54) METHODS AND COMPOSITIONS FOR BONE AND CARTILAGE REPAIR

(75) Inventors: Graham Matheson, Cronulla (AU); William Walsh, Randwick (AU)

(73) Assignee: CIMTECH PTY LIMITED, Newcastle West, New South Wales (AU)

( * ) Notice: Subject to any disclaimer, the term of this patent is extended or adjusted under 35 U.S.C. 154(b) by 897 days.

(21) Appl. No.: 13/514,249

(22) PCT Filed: Dec. 10, 2010

(86) PCT No.: PCT/AU2010/001679
§ 371 (c)(1),
(2), (4) Date: Nov. 19, 2012

(87) PCT Pub. No.: WO2011/069214
PCT Pub. Date: Jun. 16, 2011

(65) Prior Publication Data
US 2013/0071359 A1    Mar. 21, 2013

(30) Foreign Application Priority Data
Dec. 10, 2009    (AU) ................. 2009906034

(51) Int. Cl.
*A61K 36/185* (2006.01)
*A61K 36/48* (2006.01)
*A61K 36/889* (2006.01)

(52) U.S. Cl.
CPC ............ *A61K 36/185* (2013.01); *A61K 36/48* (2013.01); *A61K 36/889* (2013.01)

(58) Field of Classification Search
None
See application file for complete search history.

(56) References Cited

U.S. PATENT DOCUMENTS

| | | | |
|---|---|---|---|
| 2003/0161858 A1* | 8/2003 | Lidgren | 424/423 |
| 2007/0142306 A1 | 6/2007 | Maurel et al. | |
| 2008/0057108 A1 | 3/2008 | Koyazounda et al. | |
| 2009/0155216 A1 | 6/2009 | Yamada et al. | |
| 2011/0282464 A1 | 11/2011 | Sargeant et al. | |
| 2013/0017239 A1 | 1/2013 | Viladot Petit et al. | |

FOREIGN PATENT DOCUMENTS

| | | | |
|---|---|---|---|
| CN | 1170580 | | 1/1998 |
| CN | 1170580 A | * | 1/1998 |
| CN | 101961431 | | 11/2011 |
| CN | 102755488 | | 11/2013 |
| EP | 1747786 | | 1/2007 |
| EP | 1906980 | | 4/2008 |
| EP | 2008661 | | 12/2008 |
| EP | 2618926 | | 7/2013 |
| EP | 2626077 | | 8/2013 |
| HU | 51322 | | 4/1990 |
| TW | 200843791 | | 11/2008 |
| WO | 2007014334 | | 2/2007 |
| WO | 2008029877 | | 3/2008 |
| WO | WO-2010-127396 | | 11/2010 |
| WO | 2012038061 | | 3/2012 |
| WO | 2012072245 | | 6/2012 |

OTHER PUBLICATIONS

Cambie et al. "Hibiscus tiliaceus" from Fijian Medicinal Plants. 1931, p. 212.*
Rosa, et al., Antioxidant and Antimutagenic Properties of *Hibiscus tiliaceus* L. Methoanolic Extract, J. Agric. Food Chem. 2006, 54, 7324-7330.
Chen, et al., A New Cytotoxic Amide from the Stem Wood of Hibiscus Tiliaceus, Letter . . . Planta Med 2006, 72:935-938.
Melecchi, et al., Optimization of the Sonication Extraction Method of *Hisbiscus tiliaceus* L. Flowers, Ultrasonics Sonochemistry 13 (2006) 242-250.
Li, et al., Structure Elucidation of a New Friedelane Triterpene from the Mangrove Plant Hibiscus Tiliaceus, Magn. Reson. Chem. 2006, 44:624-628.
International Search Report issued in PCT/AU2010/001679 on Feb. 7, 2011.
Mohammad Najmul Ghani Khan; Khazaain-al-Advia, vol. III (20th century AD), Nadeem Yunus Printer/Sheikh Mohd Basheer & Sons, Lahore, 1926 AD p. 478, 479, Formulation ID: JA6/446, Formulation Name: Rughan-e-khopra.
Mohammad Najmul Ghani Khan; Khazaain-al-Advia, vol. III (20th century AD), Nadeem Yunus Printer/Sheikh Mohd Basheer & Sons, Lahore, 1926 AD p. 479, Formulation ID: JA6/446H, Formulation Name: Dawa-e-roghan-e-kopra Brae Jild.
Mohammad Najmul Ghani Khan; Khazaain-al-Advia, vol. III (20th century AD), Nadeem Yunus Printer/Sheikh Mohd Basheer & Sons, Lahore, 1926 AD p. 478, Formulation ID: JA6/446A1, Formulation Name: Rughan-e-kopra Barae Harq-o-salaq.
Kaiyadeva; Kaiyadevanighantau—(Pathyapathyavibodhakah) Edited and translated by P.V. Sharma and Guru Prasad Sharma, Chaukhambha Orientalia, Varanasi, Edn. 1st, 1979 p. 53, Formulation ID: RS6/96A, Formulation Name: Narikela Taila.
Kali Dasa; Vaidyamanorama;—with Hindi translation : Central Council for Research in Ayureda & Siddha, Govt. of India, New Delhi, Edn. 2005 [Time of origin 13th century] p. 104, Formulation ID: RS14/441B, Formulation Name: Vranahar Taila.
Mohammad Najmul Ghani Khan; Khazaain-al-Advia, vol. III (20th century Ad), Nadeem Yunus Printer/Sheikh Mohd Basheer & Sons, Lahore, 1926 AD p. 390, Formulation ID: JA6/359X, Formulation Name: Raughan-e-kalonji.
Vagabhata; Astnga Hrdaya—(commentary by Arunadutta) edited by Bhisagacarya Harisastri Paradakara vaidya : Chaukhamba Orientalia, Varanasi, edn. 8th, 1998. [Time of origin 5th century] p. 890, Formulation ID: RS23/1712B, Formulation Name: Mukhdusikahara Lepa.
Kali Dasa; Vaidyamanorama;—with Hindi translation : Central Council for Research in Ayurveda & Siddha, Govt. of India, New Delhi, Edn. 2005 [Time of origin 13th century] p. 54, Formulation ID: RS14/222, Formulation Name: Tungadrum Yogah.

(Continued)

*Primary Examiner* — Amy L Clark
(74) *Attorney, Agent, or Firm* — K&L Gates LLP

(57) ABSTRACT

Biologically active extract of *Hibiscus tiliaceus* L. and compositions comprising the extract are described. The invention also provides therapeutic uses of the extract and compositions, in particular for promoting healing of bone and cartilage injuries, and the promotion of bone and cartilage formation.

10 Claims, 19 Drawing Sheets

(56) References Cited

OTHER PUBLICATIONS

Bharata Bhaisajya Ratnakara—Compiled by Naginadasa Chaganalala Saha, Translated by Gopinath Gupta—vol. V : B. Jain Publishers, New Delhi, Edn. 2nd. Reprint, Aug. 1999. [This book contains back references from 1000 B.C. to 20th century] p. 272, Formulation ID: HG/842, Formulation Name: Snuhyadyamtailam (01).
Smith, et al., Flora Vitiensis Nova: A New Flora of Fiji (Spermathophytes Only), Pacific Tropical Botanical Garden, 1981, 2:417.
Whistler, et al., Traditional and Herbal Medicine in the Cook Islands, Journal of Ethnopharmacology, 1985, 13(3):239-280.
Extended European Search Report issued in EP10835314—Jul. 11, 2013.

\* cited by examiner

METHODS AND COMPOSITIONS FOR BONE AND CARTILAGE REPAIR

This application is the U.S. national phase of International Patent Application No. PCT/AU2010/001679, filed Dec. 10, 2010, which claims priority to Australian Patent Application No. 2009906034, filed Dec. 10, 2009.

FIELD OF THE INVENTION

The present invention relates generally to the use of plant extracts and compositions comprising the same for the treatment of bone and cartilage injuries, diseases or defects, the promotion of healing of bone and cartilage injuries, and the promotion of bone and cartilage formation. Particular embodiments as disclosed herein find application in, inter alia, the treatment of bone fractures and in bone formation and regeneration.

BACKGROUND OF THE INVENTION

Bone is a living tissue comprising a number of constituents including calcium carbonate, calcium phosphate, collagen and water and is continuously being replenished by resorption and deposition of bone matrix.

When a bone fractures the usual treatment is to reposition the fractured bone back into place, to stabilise the position of the bone, and then to wait for the bone healing process to occur. Bone healing is a complex process which is generally regarded as involving three phases: reactive phase, reparative phase and remodelling phase.

During the reactive phase a haematoma forms at the fracture site and inflammatory cells and fibroblasts infiltrate the bone under prostaglandin mediation. This results in the formation of granulation tissue, ingrowth of vascular tissue, and migration of mesenchymal cells. During the reparative phase, fibroblasts begin to lay down stroma that helps support vascular ingrowth. As vascular ingrowth progresses, a collagen matrix is laid down while osteoid is secreted and subsequently mineralised, which leads to the formation of a soft callus (cartilage) around the repair site. After a period of time from weeks to months the cartilage ossifies, forming a bridge of woven bone between the fracture fragments. During the remodelling phase the healing bone is restored to its original shape, structure, and mechanical strength. The remodelling phase occurs slowly over months to years, however, adequate bone strength is typically achieved in three to six months.

The healing of bone fractures is clearly a lengthy process. Notably, cartilage, unlike other connective tissues, does not contain blood vessels and therefore compared to other connective tissues, grows and repairs more slowly. Further, bone healing can be delayed or impaired when any of the healing processes do not function property or in a timely manner. This can be both a major setback to the individual and a costly clinical problem. Accordingly, approaches that speed up the body's natural process of regenerating bone and cartilage are clearly advantageous.

The present inventors have surprisingly found that plant extracts disclosed herein and compositions comprising same, promote bone and cartilage repair by inducing new bone formation and new cartilage growth.

SUMMARY OF THE INVENTION

According to a first aspect of the invention there is provided a biologically active extract of *Hibiscus tiliaceus* L.

The extract may further comprise an extract of one or more of *Vigna marina* (Burm.) Merr., *Cocos nucifera* L., or *Terminalia catappa* L.

The extract(s) may be derived from one or more of the following: bark, leaf, vine, bean, husk or nut. In one embodiment the *Hibiscus tiliaceus* L. extract is derived from bark, typically fresh crushed bark.

The extract may be prepared using and/or comprises, a plant based oil, a hydrocarbon and/or an alcohol. The plant based oil may be derived from plant seeds or fruit. In a particular embodiment the plant based oil is derived from *Cocos nucifera*. The *Cocos nucifera* oil may be, for example, virgin *Cocos nucifera* oil, refined *Cocos nucifera* oil, hydrogenated *Cocos nucifera* oil or fractionated *Cocos nucifera* oil.

According to a second aspect of the invention there is provided a composition comprising an extract according to the first aspect, and one or more pharmaceutically acceptable carriers, diluents and/or excipients.

In particular embodiments, the composition is for the treatment of bone or cartilage injury and/or the promotion of bone or cartilage formation, repair or regeneration.

The composition may be formulated so as to be suitable for administration by any route, for example topical or parenteral. Parenteral administration may comprise, for example, intraosseous infusion or intrathecal injection.

According to a third aspect of the invention there is provided a method for promoting the formation, repair or regeneration of bone or cartilage in a subject, the method comprising administering to the subject in need thereof an effective amount of an extract according to the first aspect, a composition according to the second aspect, or osteoblasts, osteoblastic progenitor cells, or bone segments or fragments cultured in the presence of said extract or composition.

The subject may be suffering from a bone or cartilage injury, defect or disease or may be susceptible or predisposed to such an injury, defect or disease. The Injury may be, for example, a bone fracture. The disease may be a degenerative bone disease, for example, osteoporosis. The subject may be undergoing or have undergone a bone or cartilage graft procedure, such as a skeletal fusion procedure, for example a spinal fusion procedure.

The osteoblasts or osteoblastic progenitor cells may be autogeneic, allogeneic or xenogeneic.

According to a fourth aspect of the invention there is provided a method for treating a bone or cartilage injury, defect or disease in a subject, the method, comprising administering to the subject an effective amount of an extract according to the first aspect, a composition according to the second aspect, or osteoblasts, osteoblastic progenitor cells, or bone segments or fragments cultured in the presence of said extract or composition.

The injury may be, for example, a bone fracture. The disease may be a degenerative bone disease, for example, osteoporosis. The extract or composition may enhance the rate or extent of healing of the injury or disease. The extract or composition may promote bone or cartilage formation, repair or regeneration.

According to a fifth aspect of the invention there is provided a method for promoting bone or cartilage growth surrounding a bone or cartilage graft or implantable device, the method comprising administering to a subject prior to, during or after a graft or implantation procedure, an effective amount of extract according to the first aspect, a composition according to the second aspect, or osteoblasts, osteoblastic progenitor cells or bone segments or fragments cultured in the presence of said extract or composition.

The graft may be an autograft or allograft. The graft procedure May be, for example, for the repair. of a bone fracture or for the purposes of skeletal fusion such as spinal fusion. The implantable device may be a bone fixation device or a prosthesis. The extract according to the first aspect, the composition according to the second aspect, or osteoblasts, osteoblastic progenitor cells or bone segments or fragments cultured in the presence of said extract or composition may be coated on to the prosthesis, used as an adjunct to a bone fixation device, or used as an adjunct to a bone cement used to anchor the prosthesis or bone fixation device.

In accordance with the above aspects and embodiments the administration to the subject may be during an arthroscopic or open surgical procedure.

According to a sixth aspect of the invention there is provided a method for the formation or growth of bone, the method comprising incubating osteoblasts, osteoblastic progenitor cells or bone segments or fragments in the presence of an effective amount of an extract according to the first aspect or a composition according to the second aspect, under conditions suitable to induce the formation or growth of bone.

BRIEF DESCRIPTION OF THE DRAWINGS

The present invention will now be described, by way of non-limiting example only, with reference to the accompanying drawings in which.

DETAILED DESCRIPTION OF THE INVENTION

Figure 1A:
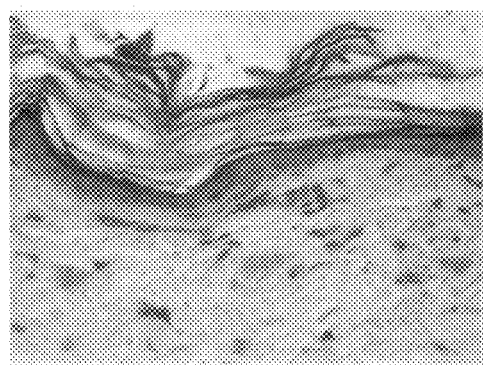
FIG. 1 shows histologic profiles of skin of 10 to 14 weeks old female rats. A, no treatment; B, daily application for 7 days of coconut oil; C, daily application for 7 days of *Hibiscus tiliaceus* L. in ethanol; and D, daily application for 7 days of *Hibiscus tiliaceus* L. in coconut oil. The skin samples were stained with hematoxylin and eosin and are shown at ×400 magnification.
Figure 1B:
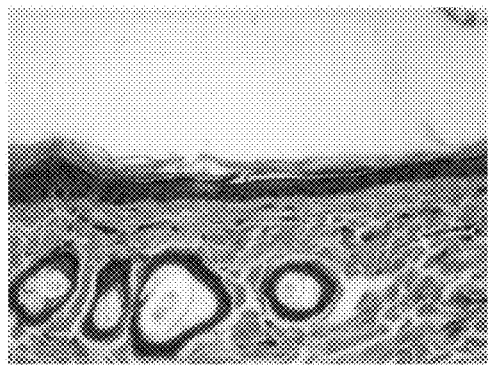
Figure 1C:
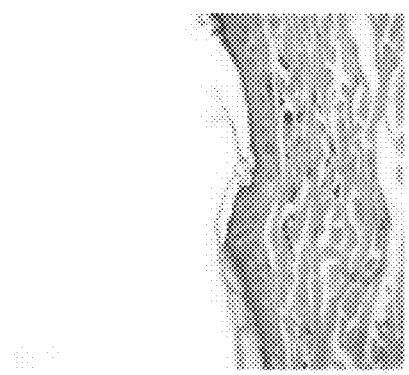
Figure 1D:
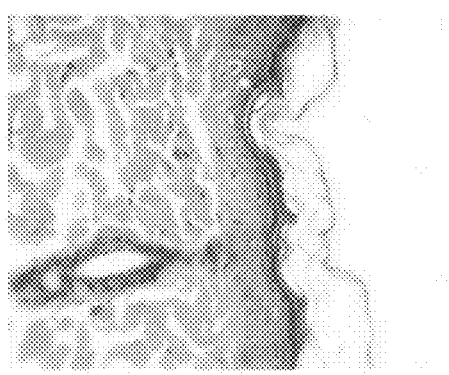
Figure 2A:
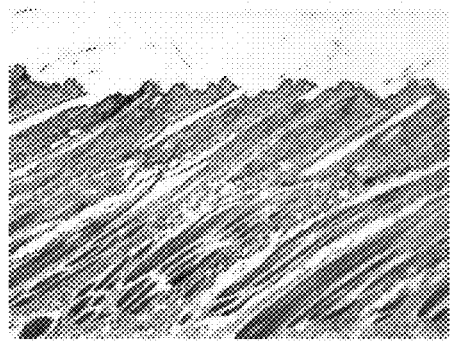
FIG. 2 shows histologic profiles of skin of 12 week old female New Zealand rabbits. A and B, no treatment; C and D, daily application for 7 days of a combination extract of *Vigna marina* (Burm.) Merr., *Cocos nucifera* L., *Terminalia catappa* L. and *Hibiscus tiliaceus* L. in coconut oil; E and F, daily application for 7 days of *Hibiscus tiliaceus* L. in coconut oil. The skin samples were stained with hematoxylin and eosin and are shown at ×40 (A, C, E) and ×400 (B, D, F) magnification.
Figure 2B:
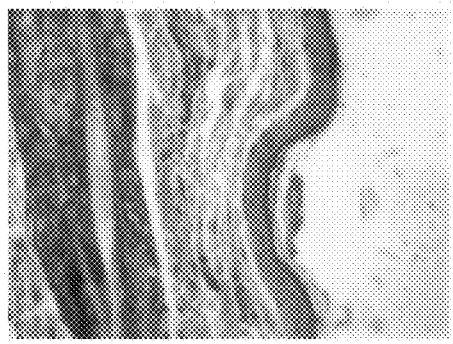
Figure 2C:
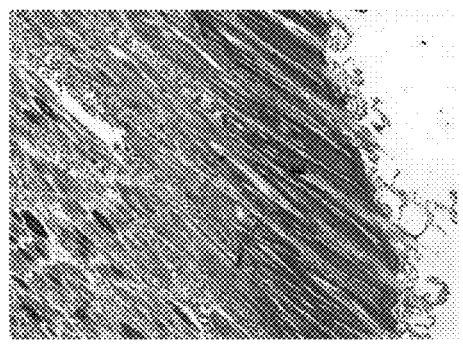
Figure 2D:
Figure 2E:
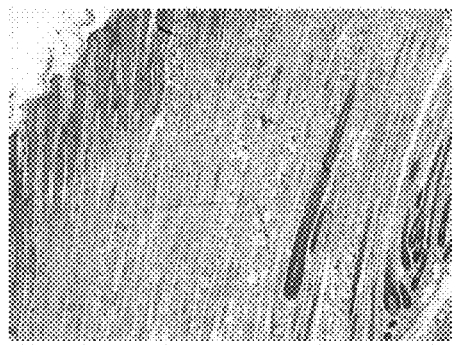
Figure 2F:
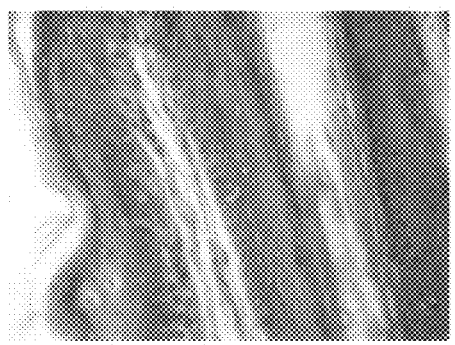
Figure 3A:
FIG. 3 shows histologic differences in untreated (A and B) and treated (C to F) 18 month old oestrogen deficient (ovaries removed at age 6 weeks) rats; and untreated (G to H) 18 month old non-oestrogen deficient (control surgical procedure carried out at age 6 weeks and rats allowed to recover) and treated rats (I to L), following a surgically created fracture of the femur by osteotomy, and operative repair with internal fixation. The treated rats were subjected to a daily application of an extract of *Hibiscus tiliaceus* L. in coconut oil to the fracture site for 21 days. The fracture histology samples were stained with hematoxylin and eosin (A, C, E, G, I, K) and Saffron-O Stain (B, D, F, H, J, L) which stains proteoglycan in cartilage purple; and are shown at ×12 magnification.
Figure 3B:
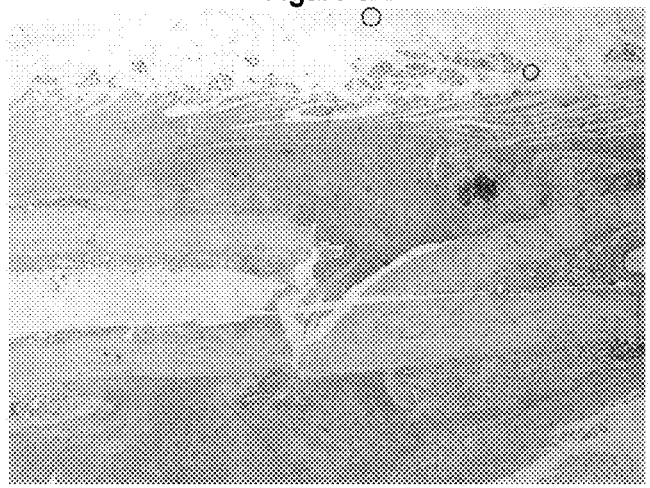
Figure 3C:
Figure 3D:
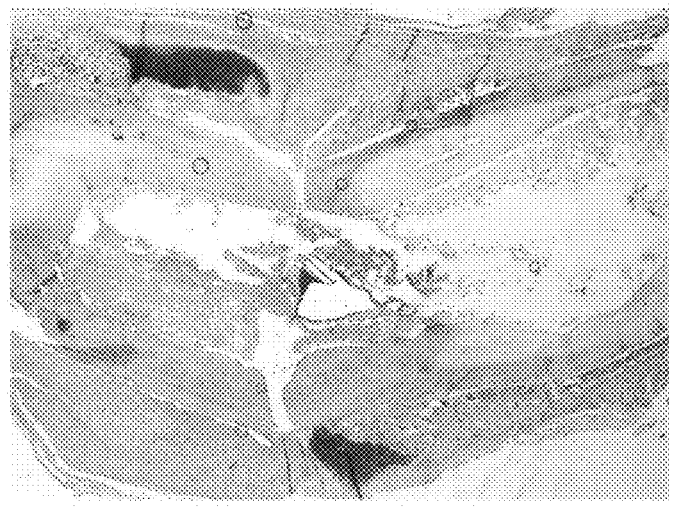
Figure 3E:
Figure 3F:
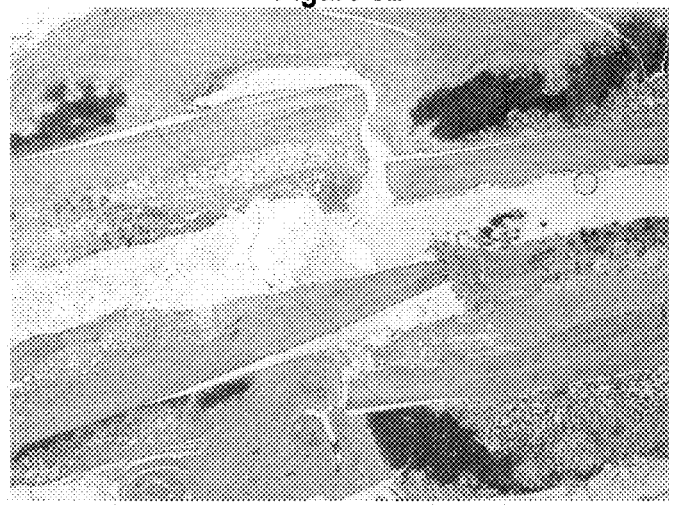
Figure 3G:
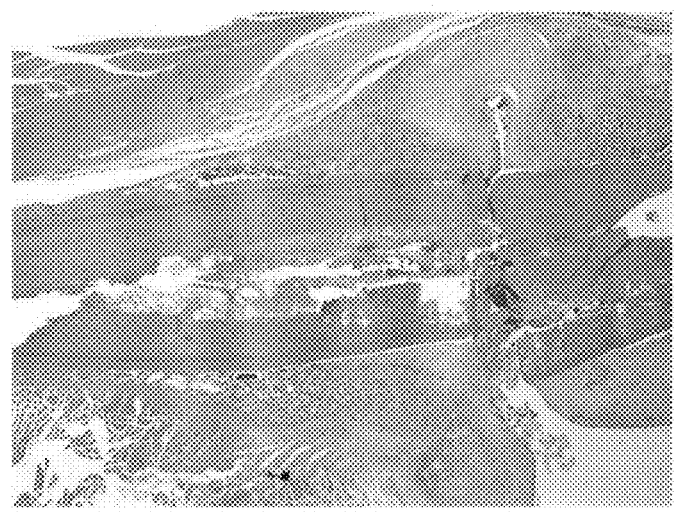
Figure 3H:
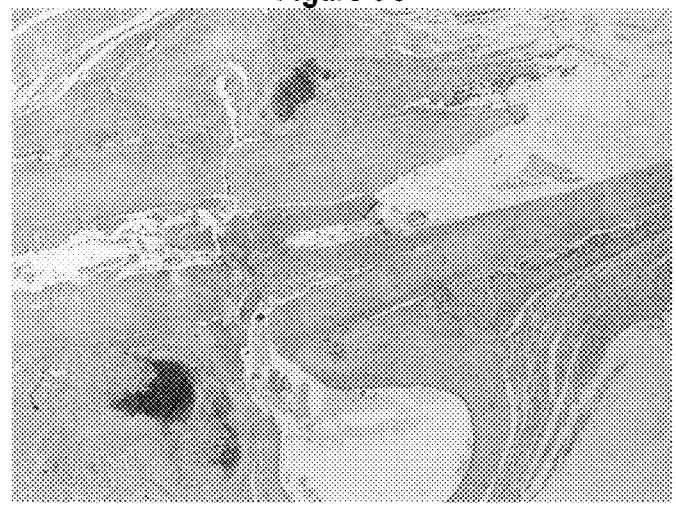
Figure 3I:
Figure 3J:
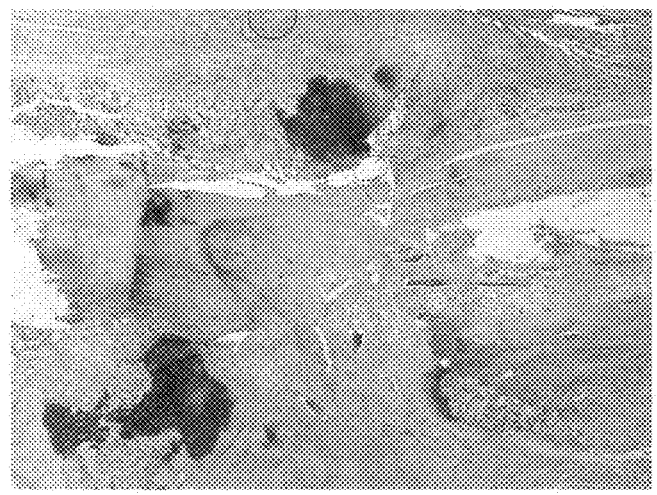
Figure 3K:
Figure 3L:
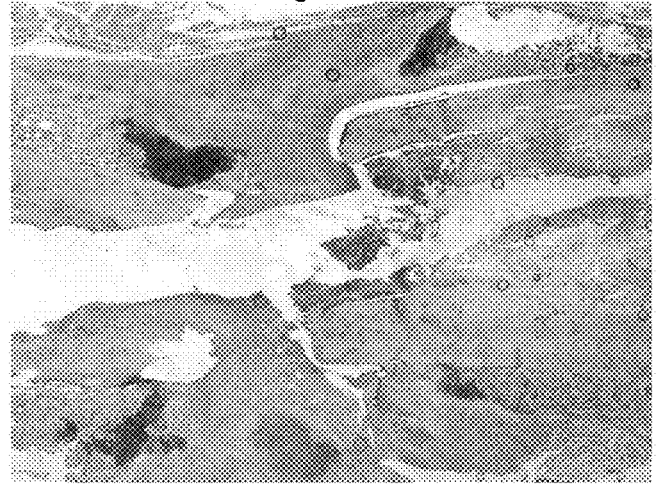

The articles "a" and "an" are used herein to refer to one or to more than one (i.e., to at least one) of the grammatical object of the article. By way of example, "an element" means one element or more than one element.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

As used herein the terms "effective amount" and "effective dose" include within their meaning a non-toxic but sufficient amount or dose of an extract or composition to provide the desired effect. The exact amount or dose required will vary from application to application and subject to subject depending on factors such as whether the extract or composition is administered in vitro, ex vivo or in vivo, the species being treated, the age and general condition of the subject, the severity of the condition being treated, the particular extract or composition being administered and the mode of administration and so forth. Thus, it is not possible to specify an exact effective amount or dose. However, for any given case, an appropriate effective amount or dose may be determined by one of ordinary skill in the art using only routine experimentation.

As used herein the term "extract" refers to an active preparation derived from one or more plants. In the context of the specification by "active" it is meant that the extract is capable of producing a desired therapeutic benefit as disclosed herein. An extract is obtained by a process of "extraction" which will be understood by those skilled in the art as, in general terms, comprising treating plant material with a solvent, a liquid, or a supercritical fluid to dissolve the active preparation and separate the same from residual unwanted plant material. An extract may be in liquid form (for example as a decoction, solution, infusion or tincture) or solid form (for example as a powder or granules). The term "combination extract" as used herein refers to an extract prepared from more than one plant species. In a combination extract the plant material from each of the plant species may be subjected to the extraction process together or separately. That is, material from some or all of the species may be combined prior to addition of the solvent, liquid or supercritical fluid, and/or material from some or all of the species may be independently treated with a solvent, liquid or supercritical fluid and the preparations so obtained are subsequently combined. As such, the same or different solvents (or liquids or supercritical fluids) may be used to extract the active preparation from the different species. The terms "extract" and "combination extract" may be used interchangeably throughout the specification.

The terms "promoting", "promotion" and variations thereof as used in the context of bone or cartilage formation, repair and regeneration refer to the ability of an extract or composition as disclosed herein to induce, stimulate, enhance, or otherwise effect or cause, either directly or indirectly, the formation of new bone or cartilage, or the repair or regeneration of bone or cartilage. The promotion may occur in vivo, ex vivo or in vitro. The terms "enhancing", "enhancement" and variations thereof as used herein in the context of bone or cartilage formation, repair and regeneration refer to the ability of an extract or composition as disclosed herein to enhance or increase, either directly or indirectly, the rate or degree of action of natural physiological process(es) involved in bone or cartilage formation, repair and/or regeneration.

As used herein the term "subject" includes humans, primates, livestock animals (eg. sheep, pigs, cattle, horses, donkeys), laboratory test animals (eg. mice, rabbits, rats, guinea pigs), companion animals (eg. dogs, cats), show animals (eg. dogs, cats, pigs, cattle, sheep, horses) and captive wild animals (eg. foxes, kangaroos, deer). Typically, the subject is human or a laboratory test animal. Even more typically, the subject is a human.

As used herein the terms "treating", "treatment", "preventing" and "prevention" refer to any and all uses which remedy a condition or symptoms, prevent the establishment of a condition or disease, or otherwise prevent, hinder, retard, or reverse the progression of a condition or disease or other undesirable symptoms in any way whatsoever. Thus the terms "treating" and "preventing" and the like are to be considered in their broadest context. For example, treatment does not necessarily imply that a patient is treated until total recovery.

In the context of this specification, the term "pharmaceutically acceptable" means that the compound to which it refers is suitable for use in contact with tissues of the body without undue toxicity, incompatibility, instability, irritation, allergic response, and the like, commensurate with a reasonable benefit/risk ratio.

The present invention is predicated on the inventors' surprising finding, as exemplified herein, that the use of extracts of various plants from Pacific islands possess biological activity when administered to mammalian skin, promoting bone and cartilage repair and the formation of new bone and cartilage.

Accordingly, provided herein are biologically active extracts of *Hibiscus tiliaceus* L. and compositions comprising the same.

While exemplified using extracts of *Hibiscus tiliaceus*, it is also contemplated that the extract may also be derived from one or more of any *Hibiscus* sp. including but not limited to, *Hibiscus acetosella, Hibiscus brackenridgei, Hibiscus cannabinus, Hibiscus diversifolius, Hibiscus lavaterioide, Hibiscus ludwigii, Hibiscus macrophyllus, Hibiscus macropodus, Hibiscus elatus, Hibiscus escobariae, Hibiscus ficulneus, Hibiscus paramutabilis, Hibiscus pedunculatus, Hibiscus platanifolius, Hibiscus radiatus, Hibiscus rosa-sinensis, Hibiscus sabdariffa, Hibiscus schizopetalus, Hibiscus scottii, Hibiscus socotranus, Hibiscus sinosyriacus, Hibiscus splendens, Hibiscus stenanthus, Hibiscus striatus, Hibiscus syriacus, Hibiscus trilobus*, or *Hibiscus waimeae*.

Extracts and compositions in accordance with some embodiments may further comprise extracts of *Vigna* sp. and/or *Terminalia* sp. In particular embodiments, the *Vigna* sp: is *Vigna marina* (Burm.) and/or the *Terminalia* sp. is *Terminalia catappa*.

It is also contemplated that the *Vigna* sp. extract may be derived from one or more of, but not limited to, *Vigna aconitifolia, Vigna angularis, Vigna caracalla, Vigna debilis, Vigna dinteri, Vigna lanceolata, Vigna luteola, Vigna maritime, Vigna mungo, Vigna o-wahuensis, Vigna parkeri, Vigna radiata, Vigna speciosa, Vigna subterranea, Vigna trilobata, Vigna umbellata, Vigna unguiculata* or *Vigna vexillate*.

It is also contemplated that the *Terminalia* sp. extract may be derived from one or more of, but not limited to, *Terminalia acuminate, Terminalia alata, Terminalia altissima, Terminalia amazonia, Terminalia angustifolia, Terminalia arborea, Terminalia arbuscula, Terminalia archipelagi, Terminalia arjuna, Terminalia australis, Terminalia avicennioides, Terminalia bellirica, Terminalia bialata, Terminalia brachystemma, Terminalia brassii, Terminalia bucidoides, Terminalia buceras (Bucida buceras), Terminalia bursarina, Terminalia calamansanai, Terminalia chebula, Terminalia cherrieri, Terminalia ciliate, Terminalia citrina, Terminalia copelandii, Terminalia corticosa, Terminalia eddowesii, Terminalia edulis, Terminalia elliptica, Terminalia eriostachya, Terminalia erythrophylla, Terminalia ferdinandiana, Terminalia foetidissima, Terminalia franchetii, Terminalia glabrescens, Terminalia glaucifolia, Terminalia hararensis, Terminalia hecistocarpa, Terminalia intermedia, Terminalia ivorensis, Terminalia januariensis, Terminalia kaernbachii, Terminalia kangeanensis, Terminalia kuhlmannii, Terminalia latifolia, Terminalia mantaly, Terminalia molinetii Terminalia muelleri, Terminalia myriocarpa, Terminalia nitens, Terminalia novocaledonica, Terminalia oblongata, Terminalia obovata, Terminalia oliveri, Terminalia paniculata, Terminalia parviflora, Terminalia pellucida, Terminalia phanerophlebia, Terminalia phellocarpa, Terminalia prunioides, Terminalia reitzii, Terminalia rerei, Terminalia schimperiana, Terminalia sericea, Terminalia seriocarpa, Terminalia subspathulata, Terminalia superba, Terminalia tripteroides* or *Terminalia volucris*.

Also provided are methods for the promotion or enhancement of bone or cartilage formation, repair or regeneration employing extracts and compositions as disclosed herein. Such methods find application in, inter alia, the treatment of bone or cartilage injuries, defects or diseases. The injury, defect or disease may be acute or chronic. Those skilled in the art will readily appreciate the scope of injuries, defects and diseases to which the embodiments disclosed herein relate, being those in which the formation of new bone or cartilage, the repair of damaged or otherwise defective bone or cartilage, or the regeneration of bone or cartilage is desirable or advantageous. By way of example only, the injury may be, for example, the result of trauma such as a bone fracture or meniscal injury. By way of example, defects and diseases include congenital bone defects, bone or spinal deformation, osteosarcoma, bone dysplasia, osteoporosis, osteomalacia (rickets), osteogenesis imperfecta (brittle bone disorder), Paget's disease of the bone, osteoarthritis, and other diseases and conditions characterised by or associated with abnormal bone metabolism, formation or resorption.

Embodiments as disclosed herein also find application in the context of surgical procedures to correct bone injuries, deformations or diseases where the promotion or enhancement of bone growth or regeneration is advantageous. For example, the embodiments disclosed herein may be used in conjunction with a skeletal fusion (e.g. spinal fusion) procedure, spinal disc reconstruction or removal, or the implantation of bone filling material (such as hydroxyapatite blocks, demineralised bon matrix plugs, collagen matrices), a fixation device (such as a rod, screw, pin, plate or the like), surgical implant or prosthetic device (such as a prosthetic hip or knee), or with a bone cement (such as that used to fill a space between a bone and a prosthetic device or to anchor a prosthetic device to a bone). The implanted material, implant or device may be resorbable or non-resorbable.

In particular embodiments application of extracts and compositions for the purposes of treating bone injuries, defects and disorders may be achieved using ex vivo procedures. For example, in the case of injuries such as bone fractures, a bone fragment(s) or bone segment(s) may be removed from the subject to be treated and cultured ex vivo with an extract or composition as disclosed herein. The bone fragment(s) or bone segment(s) and extract or composition may also be cultured together with a bone fixation device or a prosthesis if appropriate. Following culture under suitable conditions and for a suitable period of time, to at least initiate bone formation, repair or regeneration, the bone fragments) or bone segment(s), and optionally the bone fixation device or prosthesis may be reintroduced into the subject. The culture conditions will depend on the application, however suitable conditions can be readily determined by a person skilled in the art without the need for undue experimentation. Alternatively, circumstances may necessitate the use of bone fragment(s) or segment(s) from other individuals or organisms.

Similarly, osteoblasts or osteoblastic progenitor cells may be cultured ex vivo with an extract or composition as disclosed herein prior to their introduction into a subject in need of treatment. The cells may be autologous (autogeneic), allogeneic or xenogeneic. Ex vivo cell therapy may also be employed using mesenchymal stem cells taken from, for example, bone marrow or adult peripheral blood, embryonic stem cells, adult stem cells or any other multipotent, pluripotent or totipotent cells, or 'designer' cells generated in vitro. The term "osteoblastic progenitor cells" as used herein encompasses all multipotent, pluripotent and totipotent cells, whether naturally-derived or artificially created, that have the ability to differentiate into osteoblasts.

Extracts of the invention may be aqueous, oil and/or organic solvent based extracts, obtained by single, combined and/or successive extraction of any available plant material such as leaves, roots, bark, stems, fruits, shoots, nuts, husks of nuts, seeds, seed capsules, kernels, flowers, vine and/or wood. Suitable extraction processes, and suitable solvents and liquids for extraction are known to those skilled in the art. Aqueous solvents (for example water, acids, bases); oils (for example oil derived from *Cocos nucifera*); and organic solvents, which can be polar (such as alcohols for example ethanol), non-polar (for example hexane) and/or halogenated (for example dichloromethane), used for extraction can either be used sequentially for extraction or in combination mixture. Importantly, as exemplified herein, the activity of the extract is maintained when extracted into *Cocos nucifera* oil, polar solvents (e.g. ethanol) or non-polar solvents (e.g. isopentane). Supercritical fluid extraction using, for example, supercritical nitrogen or carbon dioxide, may also be used in accordance with the invention to obtain extracts.

Further, it will be appreciated by those skilled in the art that an extract of the invention may be subjected to one or more post extraction steps to, for example, increase or maintain the stability of the extract, modify or change the physical form of the extract or assist in formulating the extract into a composition for administration to a subject. By way of example only a liquid form extract may be lyophilised to produce a solid form of the extract.

Extracts of the present invention may be derived from any suitable plant material. Suitable plant material includes leaves, roots, bark, stems, fruits, shoots, nuts, husks of nuts, seeds, seed capsules, kernels, flowers, vine or wood. The plant material may be, for example, fresh, dried or freeze dried. For any given plant species more than one plant material may be used for the production of extracts. Where derived from *Hibiscus tiliaceus* L., typically the extract is a leaf, vine and/or bean extract.

Extract(s) of the invention may be administered in accordance with the present invention in the form of pharmaceutical compositions, which compositions may comprise one or more pharmaceutically acceptable carriers, excipients or diluents. Extracts may further be combined with other therapeutic agents for example, but not limited to, antibiotics, antimicrobial agents, antiseptics, anaesthetics, and/or other bone or cartilage growth or repair promoting agents.

It will be understood that the specific dose level of a composition of the invention for any particular individual will depend upon a variety of factors including, for example, the activity of the specific extract(s) employed, the age, body weight, general health and diet of the individual to be treated, the time of administration, the stability of the extract(s), the site of application on the body, and combination with any other treatment or therapy. Single or multiple administrations can be carried out with dose levels and pattern being determined as required depending on the circumstances and the individual to be treated. Suitable dosage regimes can readily be determined by the skilled addressee. A broad range of doses may be applicable. Considering a human subject, for example, from about 0.1 mg to about 1 mg of extract may be administered per kilogram of body weight per day. Dosage regimens may be adjusted to provide the optimum therapeutic response. For example, several divided doses may be administered hourly, daily, weekly, monthly or at other suitable time intervals or the dose may be proportionally reduced as indicated by the exigencies of the situation.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

The extract may be present in an amount between about 0.001% (w/w) and about 15% (w/w), or between about 0.001% and about 12%, or between about 0.001% and about 10%, or between about 0.005% and about 10%, or between about 0.01% and about 10%, or between about 0.05% and about 10%, or between about 0.05% and about 5% in the topical composition.

Compositions as disclosed herein may be administered via any convenient or suitable route such as for example by parenteral, topical, oral, or nasal routes. Parenteral administration may comprise, for example, intraosseous infusion, or inthrathecal, intravenous, intraarterial, intramuscular, or subcutaneous administration. In some embodiments, treatment may be effected using methods and compositions as disclosed herein during arthroscopic or open surgical procedures.

Topical formulations typically comprise one or more extracts of the invention together with one or more acceptable carriers, and optionally any other therapeutic ingredients. Formulations suitable for topical administration may be in any suitable form, formulated for example as liniments, lotions, creams, gels, ointments or pastes. Examples of pharmaceutically acceptable carriers or diluents are demineralised or distilled water; saline solution; vegetable based oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

Lotions according to the present invention include those suitable for application to the skin or to an epidermal appendage. Lotions or liniments for application to the skin may also include an agent to hasten drying and to cool the skin, such as an alcohol or acetone, and/or a moisturiser such as glycerol, or oil such as coconut oil, castor oil or arachis oil.

Creams, ointments or pastes according to the present invention are semi-solid formulations of the extract for external application. They may be made, by mixing the extract in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as coconut, almond, corn, arachis, castor or olive oil; wool fat or its derivatives, or a fatty acid such as stearic or oleic acid together with an alcohol such as propylene glycol or macrogols.

The compositions of the invention may be included in topical vehicles in an amount between about 0.001% (w/w) and about 90% (w/w), or between about 1% (w/w) and about 50% (w/w), or between about 1% (w/w) and about 40% (w/w), or between about 1% (w/w) and about 20% (w/w) or about 0.01%, 0.5%, 1%, 2%, 3%, 4%, 5%, 6%, 7%, 8%, 9%, 10%, 11%, 12%, 13% 14%, 15%, 16%, 17%, 18%, 19%, 20%, 25%, 30%, 35%, 40%, 45%, 50%, 55%, 60%, 65%, 70%, 75%, 80%, 85%, 90%.

The extracts and/or compositions also may be impregnated in any form into transdermal patches, plasters, and dressings such as bandages or hydrocolloid dressings, for example in liquid or semi-liquid form.

The extracts and/or compositions may also be coated on to or used as an adjunct to a bone fixation device, a prosthesis or a bone cement. The extracts and/or compositions may also be used as an additive to a bone graft extender or bone substitute, for example, allograft bone, hydroxyapatite, wollanosite or tricalcium phosphate.

In particular circumstances, for example in the post surgical promotion of bone and cartilage formation, repair or regeneration, administration of compositions by parenteral administration, typically injection, may be appropriate. Pharmaceutical forms suitable for injectable use include sterile aqueous solutions (where water soluble) or dispersions and sterile powders for the extemporaneous preparation of sterile injectable solutions. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised extract(s) into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the extract plus any additional desired extract from previously sterile-filtered solution thereof.

The compositions of the invention may also be conveniently presented in unit dosage form and prepared by any of the methods well known in the art of pharmacy. The method may include the step of bringing the components of the oral composition into association with a carrier which constitutes one or more accessory ingredients. In general, the compositions are prepared by uniformly and intimately bringing into association the components of the oral composition with a liquid carrier or finely divided solid carrier, or both and then, if necessary, shaping the product into the desired composition.

Compositions suitable for oral administration may be presented as discrete units (i.e. dosage forms) such as gelatine or HPMC capsules, cachets or tablets, each containing a predetermined amount each component of the composition as a powder, granules, as a solution or a suspension in an aqueous liquid or a non-aqueous liquid, or as an oil-in-water liquid emulsion or a water-in-oil liquid emulsion.

When the composition is formulated as capsules, the components of the oral composition may be formulated with one or more pharmaceutically acceptable carriers such as starch, lactose, microcrystalline cellulose and/or silicon dioxide. Additional ingredients may include lubricants such as magnesium stearate and/or calcium stearate.

Tablets may be prepared by compression or moulding, optionally with one or more accessory ingredients. Compressed tablets may be prepared by compressing in a suitable machine the components of the oral composition in a free-flowing form such as a powder or granules, optionally mixed with a binder, lubricant (for example magnesium stearate or calcium stearate), inert diluent or a surface active/dispersing agent Moulded tablets may be made by moulding a mixture of the powdered composition moistened with an inert liquid diluent, in a suitable machine. The tablets may optionally be coated, for example, with an enteric coating and may be formulated so as to provide slow or controlled release of the composition therein.

The present invention contemplates combination therapies, wherein extracts or compositions as described herein are coadministered with other suitable agents or treatments which may facilitate the desired therapeutic effect. For example, one may seek to administer antibiotics, antimicrobial agents, anaesthetics, analgesics, or other bone or cartilage growth- or repair-promoting agents in combination with extracts or compositions disclosed herein. By "coadministered" is meant simultaneous administration in the same formulation or in two different formulations via the same or different routes or sequential administration by the same or different routes. By "sequential" administration is meant a time difference of from seconds, minutes, hours or days between the administration of the two types of agents. The agents may be administered in any order. For example, embodiments of the present invention contemplate the administration of a lipid or an oil, for example *Cocos nucifera* oil prior to, or after, the extract or composition is administered.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be described with reference to the following specific examples, which should not be construed as in any way limiting the scope of the invention.

EXAMPLES

Example 1—Preparation of a Combination Extract of *Vigna marina* (Burm.) Merr., *Cocos nucifera* L, *Terminalia catappa* L. and *Hibiscus tiliaceus* L. In Coconut Oil Coconut oil (200 mL) was added to fresh shredded leaves of *Vigna marina* (Burm.) Merr. (100 g) and fresh shredded leaves of *Terminalia catappa* L. (100 g). The mixture was placed in a crucible in a water bath at 100° C. for 20 min. The mixture was removed from the heat and immediately filtered and pressed to extract the coconut oil. The resultant coconut oil, containing extracts of *Vigna marina* (Burm.) Merr. and *Terminalia catappa* L., was added to the fresh crushed husk of a green nut of *Cocos nucifera* L. (100 g) and the shaved bark of *Hibiscus tiliaceus* L. (100 g). The mixture was left to settle for 4 h and then filtered and pressed to extract the coconut oil.

The coconut oil was then inverted and stored at less than 20° C. until the coconut oil solidified. Any remaining moisture or solid in the mixture were removed by decanting from the solidified coconut oil. The coconut oil was then heated in a hot water bath at approximately 56° C. and filtered. The resultant filtrate contained a combination extract of *Vigna marina* (Burm.) Merr., *Cocos nucifera* L., *Terminalia catappa* L. and *Hibiscus tiliaceus* L.

Example 2—Preparation of Extracts of *Hibiscus tiliaceus* L 2.1 *Hibiscus tiliaceus* L. Extract in Coconut Oil The fresh crushed bark of *Hibiscus tiliaceus* L. (100 g) were immersed in coconut oil (100 mL). The extract was prepared by cold pressing the *Hibiscus tiliaceus* L. and coconut oil mixture; or by heating the mixture. The cold pressing was carried out by placing the *Hibiscus tiliaceus* L. and coconut oil mixture inside a new coffee plunger and leaving the mixture to settle for 1 h, the plunger was then depressed thereby extracting the oil. The mixture was left to settle for a further 5 min and the plunger depressed again to release more oil. This process was repeated 5 times until no further oil was obtained. When the extract was prepared by heating, the *Hibiscus tiliaceus* L. and coconut oil mixture was heated in a crucible in a water bath at 100° C. for 20 min, removed from the heat, and then immediately filtered and pressed to extract the coconut oil. Any remaining moisture or solid in the extract after cold pressing or heating and filtering were removed by inverting the coconut oil extract and storing it at less than 20° C. until the coconut oil solidified and then decanting the solidified coconut oil; or by decanting in a separating funnel.

2.2 *Hibiscus tiliaceus* L. Extract in Coconut Oil Following Extraction in Ethanol The fresh crushed bark of *Hibiscus tiliaceus* L. (1000 g) were immersed in 95-100% ethanol (2000 mL) and left to steep for 6 h. The ethanol was then removed and the *Hibiscus tiliaceus* L. steeped in a second aliquot of ethanol (2000 mL) for a further 6 h. The resultant ethanol extracts were added to coconut oil (250 mL). More than half the volume of ethanol was removed by heating above the boiling point of ethanol. The coconut oil was then extracted by decanting from the solution following standing for at least 2 h in a decanting vessel; or by inverting the coconut oil extract and storing it at less than 20° C. until the coconut oil solidified and then decanting the solidified coconut oil.

2.3 *Hibiscus tiliaceus* L. Extract in Coconut Oil Following Extraction in Ethanol and Hydrocarbon The fresh crushed bark of *Hibiscus tiliaceus* L. (1000 g) were immersed in 95-100% ethanol (2000 mL) and left to steep for 6 h. The ethanol was then removed and the *Hibiscus tiliaceus* L. steeped in a second aliquot of ethanol (2000 mL) for a further 6 h.

The resultant ethanol solution was agitated with hexane, pentane, methyl butane or an equivalent hydrocarbon or fluoro/chloro/bromo-hydrocarbon (250 mL). The hydrocarbon layer and oily foam layer were decanted from the solution following standing for at least 2 h in a decanting vessel; or by the dilution of the ethanol solution from 95% to a lower concentration, nominally but not necessarily 50% ethanol and then decanted after settling of the layers. Water (250 mL) or alcohol (250 mL) was added to the extracted hydrocarbon layer. To this coconut oil (250 mL) was added and the mixture agitated and allowed to settle. The hydrocarbon was removed from heating the mixture to the boiling point of the hydrocarbon.

2.4 *Hibiscus tiliaceus* L. Extract in Coconut Oil Following Extraction in Ethanol The fresh crushed bark of *Hibiscus tiliaceus* L. (1000 g) were immersed in 95-100% ethanol (2000 mL) and left to steep for 6 h. The ethanol was then removed and the *Vigna marina* (Burm.) Merr. steeped in a second aliquot of ethanol (2000 mL) for a further, 6 h. The resultant ethanol solution was agitated with coconut oil (250 mL): The hydrocarbon was decanted from the solution following standing for at least 2 h in a decanting vessel; or by the dilution of the ethanol solution from 95% to a lower concentration, nominally but not necessarily 50% ethanol and then decanted after settling of the layers. The decanting of the coconut oil may be facilitated by the addition of a low boiling point hydrocarbon to the mixture as it agitates and settles. The coconut oil was then inverted and stored at less than 20° C. until the coconut oil solidified, or by decanting in s separation vessels.

Example 3—Effect of Individual Extracts of *Hibiscus tiliaceus* L. On Skin

An assessment of the activity of the extracts prepared as described in Example 2 on skin was carried out. A daily dose of 1 mL of *Hibiscus tiliaceus* L. extract in coconut oil (Example 2.1) and 1 mL of *Hibiscus tiliaceus* L extract in ethanol (Example 2.2). The extracts were applied topically to the epithelial surface of the backs of 10-14 week old female rats. The controls were 10-14 week old female rats treated daily with 1 mL of coconut oil or left untreated.

FIGS. 1A to 1D show the histology of the skin at 7 days of the untreated control (1A) after a daily application of coconut oil (1B); an extract preparation of *Hibiscus tiliaceus* L in ethanol (1C); and coconut oil following extraction with ethanol (1D). The histological profiles show that the extract has limited activity in ethanol, but that in coconut oil the extract induces hypertrophy of the epithelium and the epithelial appendages in particular hair follicles.

An assessment of the activity of the extracts prepared as described in Examples 1 and 2.2 on skin was carried out. A daily dose of 1 mL of the extracts were applied topically to the epithelial surface of the backs of 12 week old, female New Zealand rabbits. The control was the untreated skin of 12 week old female New Zealand rabbits.

FIGS. 2A to 2F show the histology of the skin at 7 days of the untreated control (2A and B); and after a daily application of a combination extract of *Vigna marina* (Burm.) Merr., *Cocos nucifera* L., *Terminalia catappa* L. and *Hibiscus tiliaceus* L. in coconut oil prepared as described in Example 1 (2C and D); and *Hibiscus tiliaceus* L in coconut oil prepared as described in as Example 2.2 (2E and F). The histological profiles show that the extracts induce hypertrophy of the epithelium and the epithelial appendages in particular hair follicles.

Example 4—Treatment of Fractures in Oestrogen and Non-Oestrogen Deficient Bones

A study was carried out to assess the effect of an extract of *Hibiscus tiliaceus* L. prepared as described in Example 2.1, on bone fracture repair in oestrogen deficient and non-oestrogen deficient rats. In the study a daily dose of 1 mL of the extract was applied topically to the epithelial surface of 18 month old, oestrogen deficient (ovaries removed at age 6 weeks) rats and 18 month old rats with their ovaries intact (a control surgical procedure was carried out at age 6 weeks and the rats allowed to recover), following a surgically created fracture of the femur by osteotomy, and operative repair with internal fixation. The extract was applied daily to the test animals for a total of 3 weeks. Control animals were 18 month old, oestrogen deficient (ovaries removed at age 6 weeks) rats and 18 month old rats with their ovaries intact with no topical application of the extract. At 3 weeks the histology of the animals was assessed, with particular attention paid to the cartilage and new bone formation in the healing fracture.

FIG. 3A to 3H show the histology at the fracture site. The results indicate extensive new cartilage growth and new bone formation following the cartilage caps in the treated groups, particularly of note is the amount occurring in the oestrogen deficient bones.

Figure 4:
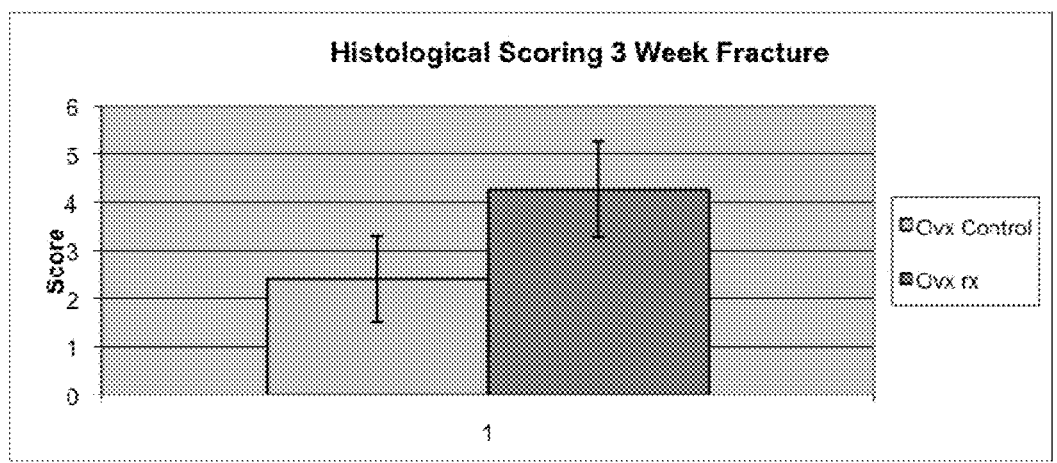
FIG. 4 shows a graph of histological scoring at the fracture sites in untreated 18 month old oestrogen deficient (ovaries removed at age 6 weeks) rats (Ovx Control) (control surgical procedure was carried out at age 6 weeks and rats allowed to recover); and treated 18 month old oestrogen deficient (ovaries removed at age 6 weeks) rats (Ovx rx) rats, following a surgically created fracture of the femur by osteotomy, and operative repair with internal fixation. The treated rats were subjected to a daily application of an extract of *Hibiscus tiliaceus* L. in coconut oil to the fracture site for 3 weeks.
Figure 5A:
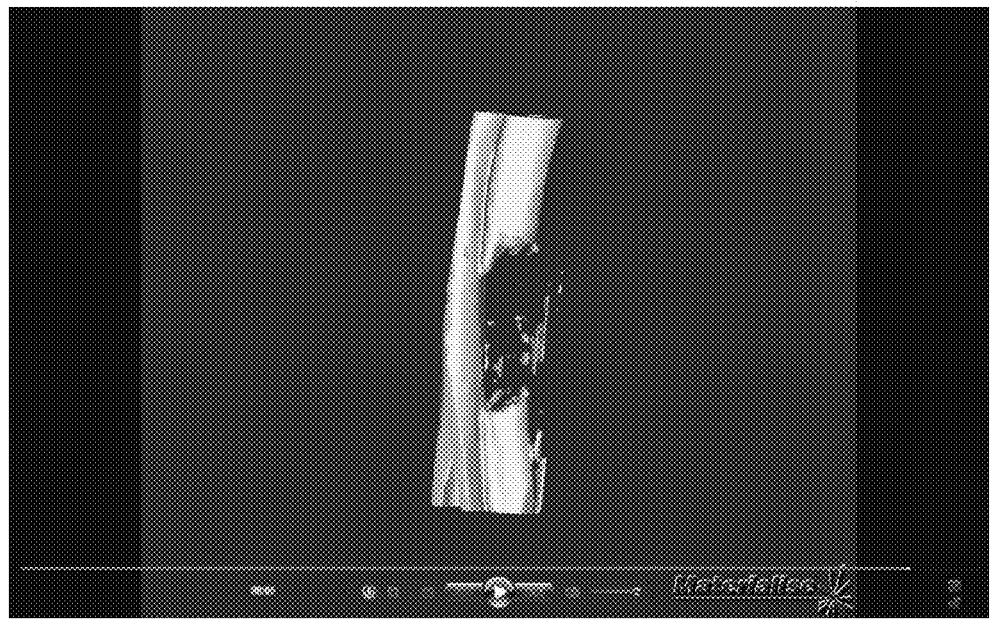
FIG. 5 shows computer models (A and C) and radiographs (B and D) of surgically created 20 mm defects of the ulna (including periosteum) by osteotomy, and with no graft or substitute filler in 12 week old NZ white rabbits, following a daily application for 7 days to the epithelial surface of the back, not on the limb of the fracture site of: A and C; coconut oil with intermediate hydrocarbon Extract and; C to D; hydrocarbon extract of *Hibiscus tiliaceus* L. in coconut oil.
Figure 5B:
Figure 5C:
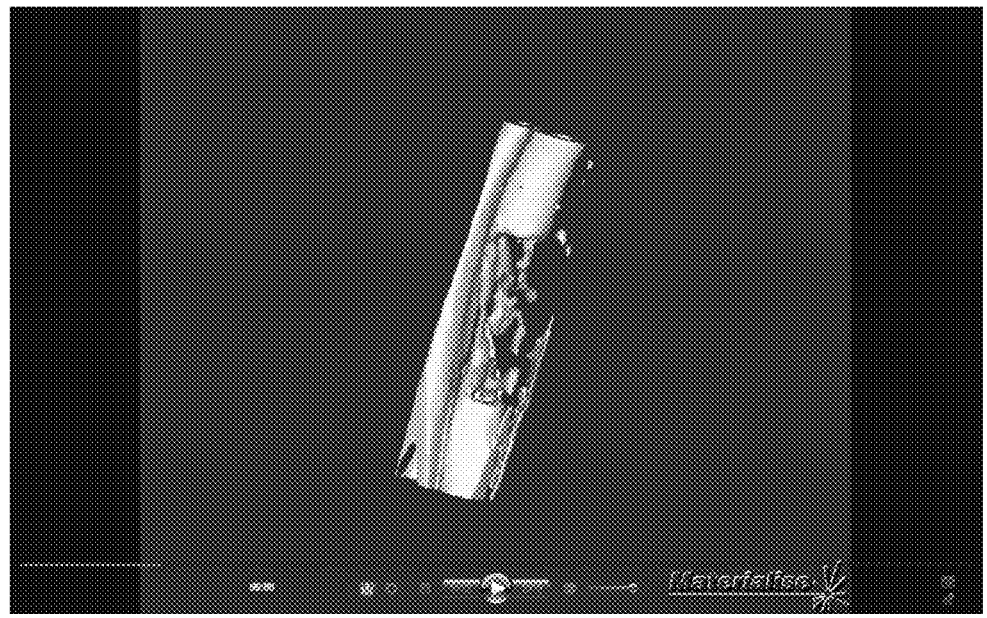
Figure 5D:
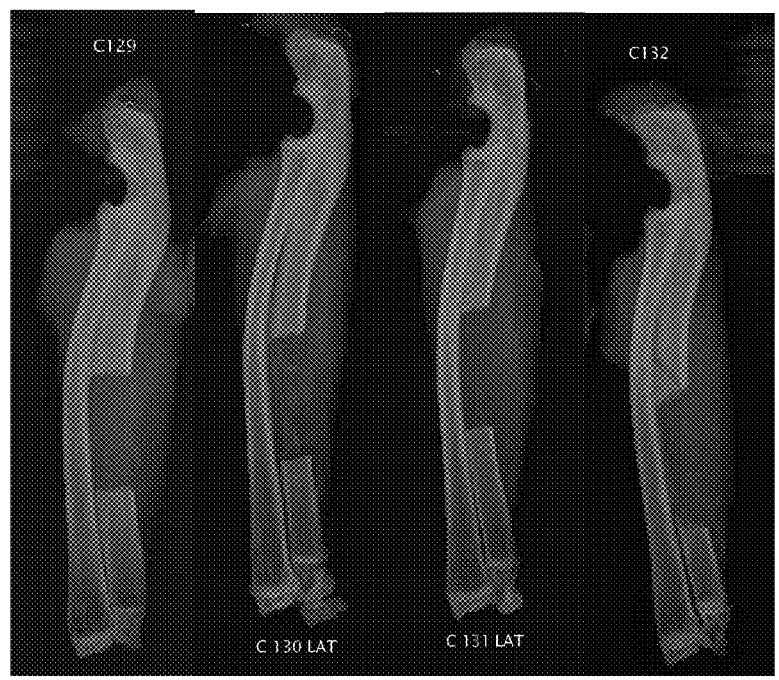
Figure 6A:
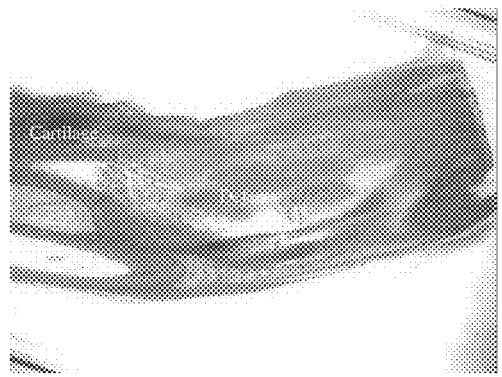
FIG. 6 shows histologic profiles in 12 week old female New Zealand rabbits following a daily application for 7 days to the epithelial surface at the fracture site (surgically created 20 mm defect of the ulna (including periosteum) by osteotomy, and with no graft or substitute filler) of: a combination extract of *Vigna marina* (Burm.) Merr, *Cocos nucifera* L., *Terminalia catappa* L. and *Hibiscus tiliaceus* L. in coconut oil (C and D); an extract of *Hibiscus tiliaceus* L. in coconut oil (E and F). A and B, untreated controls. The samples were stained with pentachrome and are shown at ×12.5 (A, C. E) and ×25 (B, D, F) magnification.
Figure 6B:
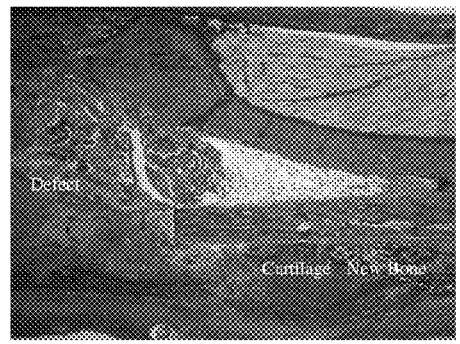
Figure 6C:
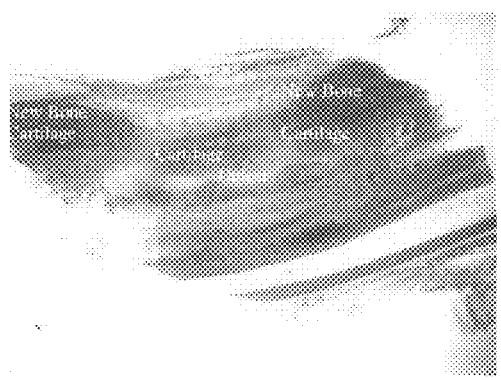
Figure 6D:
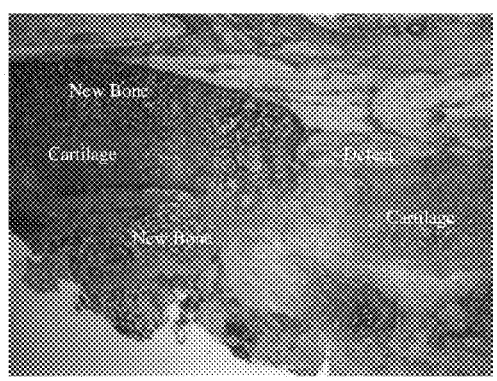
Figure 6E:
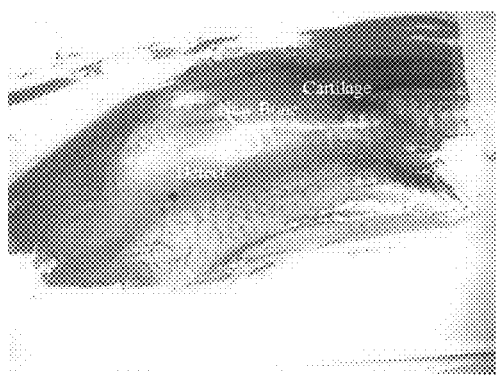
Figure 6F:
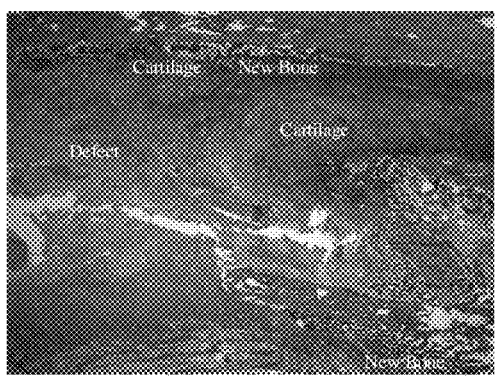
Figure 7A:
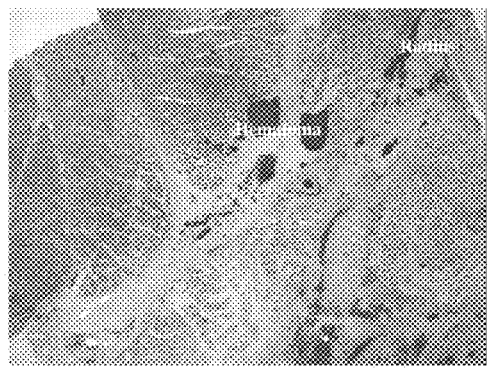
FIG. 7 shows histologic profiles in 12 week old female New Zealand rabbits following a daily application to the epithelial surface at the fracture site (surgically created surgically created 20 mm defect of the ulna (including periosteum) by osteotomy, and with no graft or substitute filler) for 7 days of: A and B, a combination extract of *Vigna marina* (Burm.) Merr., *Cocos nucifera* L., and *Terminalia catappa* L. (no *Hibiscus tiliaceus* L.) in coconut oil; C and D, an extract of *Hibiscus tiliaceus* L. in ethanol; E and F, an extract of *Hibiscus tiliaceus* L. in coconut oil following extraction in ethanol; and G and H, an extract of *Hibiscus tiliaceus* L in coconut oil following extraction in ethanol and hydrocarbon. The samples were stained with pentachrome and are shown at ×12.5 magnification.
Figure 7B:
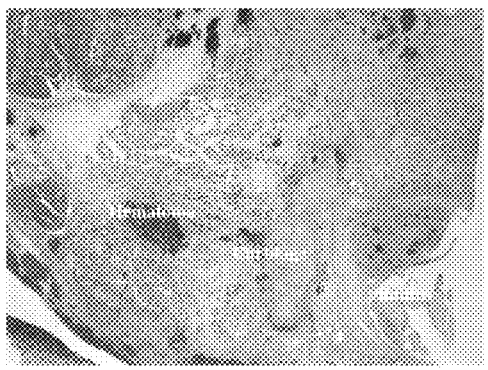
Figure 7C:
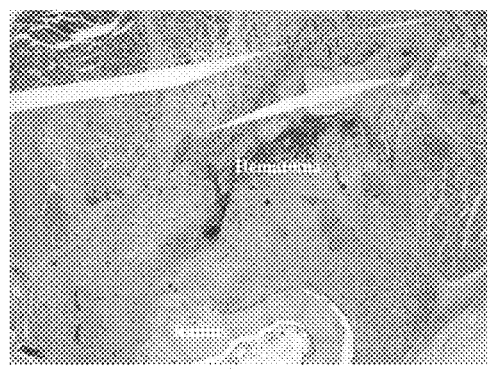
Figure 7D:
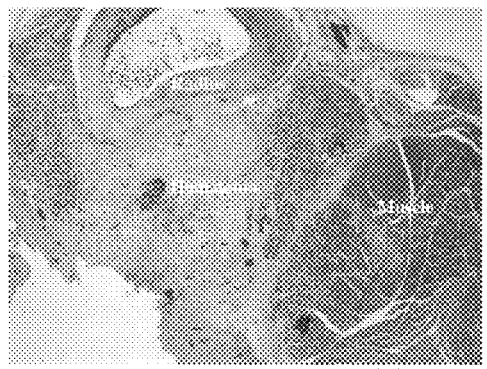
Figure 7E:
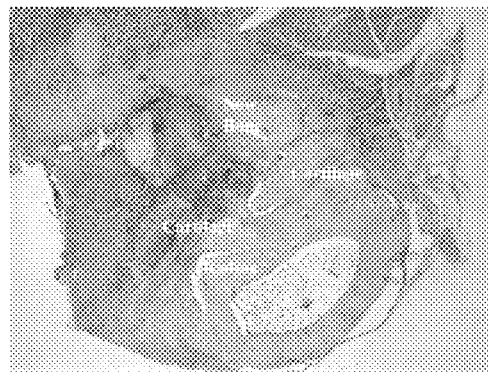
Figure 7F:
Figure 7G:
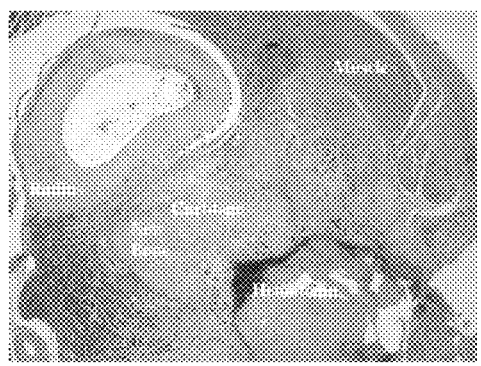
Figure 7H:
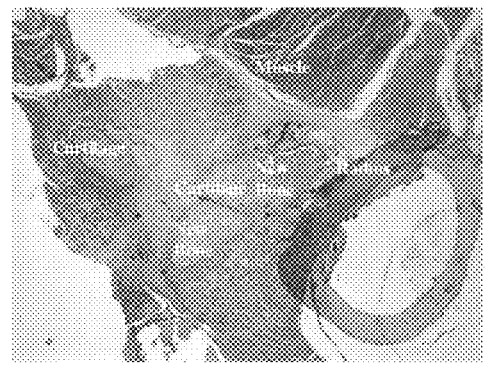

FIG. 4 is a graph showing histological scoring of the fracture sites of untreated oestrogen deficient rats (Ovx Control) and treated oestrogen deficient rats (Ovx rx) rats. In order to determine the total histological scoring the following fracture healing and tissue response parameters were scored: callous formation, bone union, marrow changes and cortex remodelling. Each parameter was scored from 0 (no callous formation; no new bone in the fracture; fibrous tissue or red; and no remodelling) to 3 (full callous formation across the defect; full bone bridge union; adult type fatty marrow; and full remodelling cortex), with a score of 1 indicating mild healing (<50%) and a score of 2 indicating moderate healing (>50% but less than full fracture healing or tissue response). After 3 weeks there was a significantly higher total histological score for the fracture healing and tissue response at the fracture sites of treated oestrogen deficient rats compared to untreated oestrogen deficient rats.

Example 5—Treatment of Fractures

A study was carried, out to assess the effect of an extract of *Hibiscus tiliaceus* L. prepared as described in Examples 1 and 2.1 on bone fracture healing. In the study a daily dose of 1 mL of the extract was applied topically to the epithelial surface of 12 week old NZ white rabbits, following a surgically created 20 mm defect of the ulna (including periosteum) by osteotomy, and with no graft or substitute filler. The extract was applied daily to the test animals for a total of 1 week. Control animals were 12 week old NZ white rabbits with no topical application of the extract. At 1 week radiology and histology of the animals was assessed, with particular attention paid to cartilage and new bone formation.

FIGS. 5A to 5D are radiographs of the bone and FIGS. 6A to 6F and 7A to 7D show histology of the bone defect at the fracture site. The figures illustrate the effect of the extracts of *Hibiscus tiliaceus* L. on the healing of the fracture. After seven days there was significantly more bone formation, new cartilage formation and greater vascularity at the fracture site than in untreated or control treatment fractions.

Figure 8:
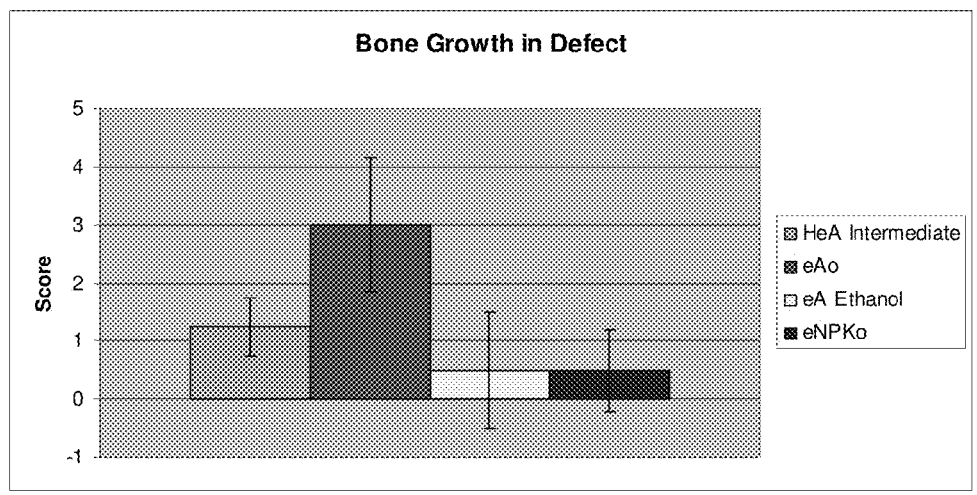
FIG. 8 shows a graph of the bone growth score in surgically created 20 mm defects of the ulna (including periosteum) by osteotomy; in 12 week old NZ white rabbits, following a daily application for 7 days to the epithelial surface at the fracture site of: *Hibiscus tiliaceus* L. precipitate of intermediate density in ethanol (HeA Intermediate); *Hibiscus tiliaceus* L in coconut oil following extraction with ethanol (eAo); *Hibiscus tiliaceus* L in ethanol (eA Ethanol); and a combination extract of *Vigna marina* (Burm.) Merr., *Cocos nucifera* L., and *Terminalia catappa* L. in coconut oil following extraction with ethanol (eNPKo).
Figure 9A:
FIG. 9 shows x-rays (A to D) and a CT scan (E) of the spine of female New Zealand rabbits which underwent bilateral single level postero-lateral fusion using autograft harvested from the iliac crest at 12 weeks old. Surgery was followed by routine care (A and B) or daily application for 5 days and then twice weekly application to 6 weeks to the epithelial surface rostral to, but not overlying the fracture site of an extract of *Hibiscus tiliaceus* L. in coconut oil following extraction in ethanol and hydrocarbon (C to E). X-Rays show the bilateral spinal repair, with A the untreated and C the treated 6 week post operative healing fusion mass, and the donor harvest site on the iliac crest in untreated (B) and treated (D) animals at 6 weeks. The CT scan shows the iliac crest of a treated animal at 6 weeks (E).
Figure 9B:
Figure 9C:
Figure 9D:
Figure 9E:

FIG. 8 is a graph of the bone growth score which shows the bone healing of the defect evaluated using a healing score definition based on the percent of bone or cartilage occupied space. The following scoring system was used: 0=no visible bone; 1=minimal (1% to 20%) new bone growth no cartilage; 2=mild (1 to 20%) cartilage with new bone growth; 3=moderate (20% to 40%) cartilage and bone growth; 4=marked (60 to 80%) cartilage and bone growth; 5=complete defect filled with new bone and cartilage; 6=defect filled with new bone and no cartilage; 7=cortical bone replacing woven bone; and 8=new marrow space forming. After 7 days there was significantly more bone formation at the fracture site treated with *Hibiscus tiliaceus* L in coconut oil following extraction with ethanol (eAo) than the fracture sites treated with *Hibiscus tiliaceus* L precipitate of intermediate density in ethanol (HeA Intermediate) in untreated or control treatment fractions; *Hibiscus tiliaceus* L in ethanol (eA Ethanol); or a combination extract of *Vigna marina* (Burm.) Merr., *Cocos nucifera* L., and *Terminalia catappa* L. in coconut oil following extraction with ethanol (eNPKo).

Example 6—Bone Formation Following a Spinal Fusion Auotgraft

A study was carried out to assess the effect of an extract of *Hibiscus tiliaceus* L. prepared as described in Example 2.4 on bone fracture repair. In the study a daily dose 1 mL of the extract was applied topically to the epithelial surface of 12 week old NZ white rabbits, following anaesthetisation and a bilateral single level postero-lateral fusion using autograft harvested from the iliac crests. The extract (5 mL) was applied daily to the test animals for 5 days and then twice weekly until sacrifice. The control animals were 12 week old NZ white rabbits with no topical application of the extract.

FIGS. 9A to 9E show x-rays and a CT scan of the spine in treated and untreated controls. The Figures show the effect of the extracts of *Hibiscus tiliaceus* L. on bone growth surrounding the site of the autograft. After only seven days there was more bone formation, new cartilage formation and greater vascularity at the fracture site than in untreated or control treatment fractures.

Figure 10A:
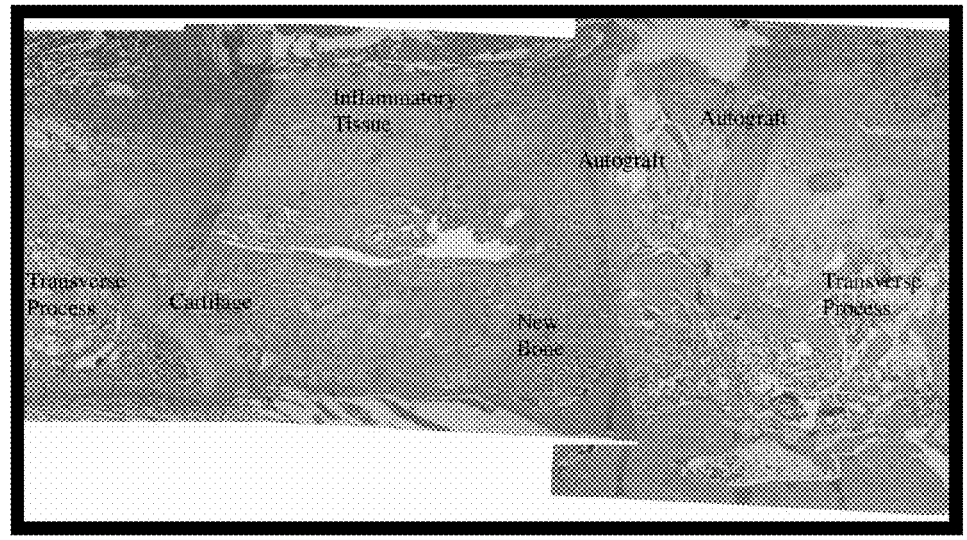
FIG. 10 shows histologic profiles of the spine of female New Zealand rabbits which underwent bilateral single level postero-lateral fusion using autograft harvested from the iliac crest at 12 weeks old. Surgery was followed by routine care (A) or daily application for 5 days and then twice weekly application to 6 weeks to the epithelial surface rostral to, but not overlying the fracture site of 5 ml of an extract of *Hibiscus tiliaceus* L. in coconut oil following extraction in ethanol and hydrocarbon (B). The samples were stained with hematoxylin and eosin and are shown as a composite of images at ×12.5 magnification showing the transverse process and the spinal fusion mass 2-3 mm lateral to the vertebral body.
Figure 10B:
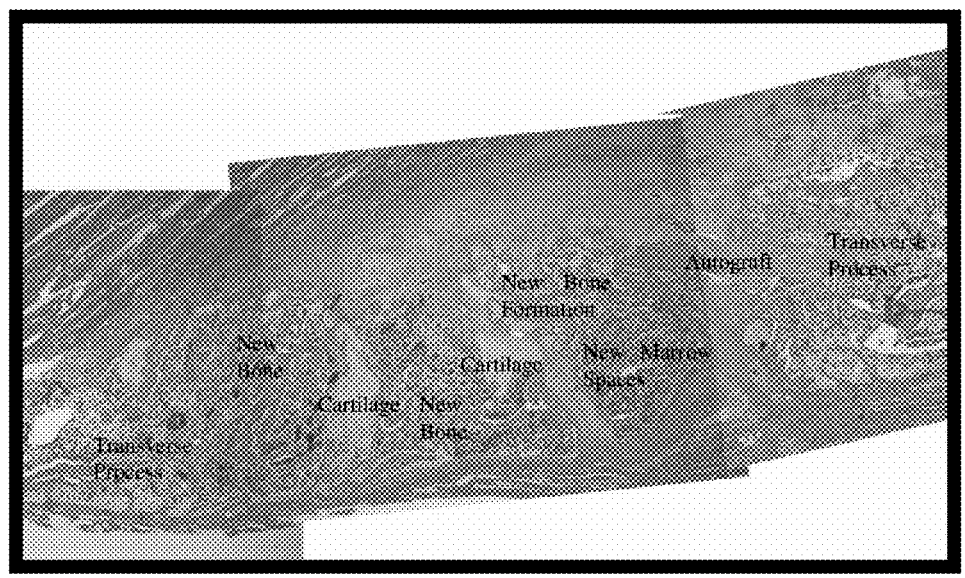

FIGS. 10A and 10B show the histology of the spine at 6 weeks. FIG. 10A shows the histology of the control autograft at 6 weeks, stained with Haematoxylin and Eosin covering the entire spinal fusion mass. The transverse processes can be seen at each end of the mass with the well formed marrow spaces and dense cortical bone (A) and adjacent to the transverse process is a small amount of cartilage (B). The bone fragments from the autograft are still visible and are necrotic, with the loss of lacunae (C). The centre of the fusion mass is predominantly fibrous tissue (D) and some new woven bone (E).

FIG. 10B shows the histology of the treated autograft at 6 weeks, stained with Haematoxylin and Eosin covering the entire spinal fusion mass. The transverse processes can be seen at each end of the mass with the well formed marrow spaces and dense cortical bone (A) and adjacent to the transverse process is corticated new bone (B). The bone fragments from the autograft are barely visible and are mostly absorbed and replaced (C). The centre of the fusion mass is predominantly cartilage (D), new marrow spaces (E) and some new woven bone (F).

Figure 11:
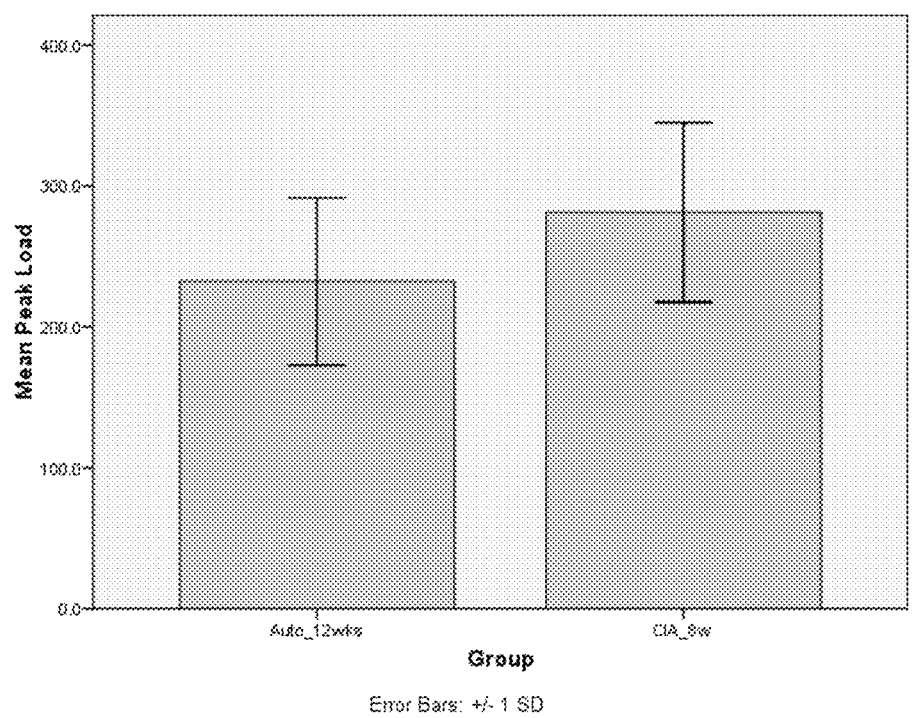
FIG. 11 show the results of mechanical testing of treated autografts at 8 weeks and untreated controls at 12 weeks.

FIG. 11 show the results of mechanical testing of the treated autograft at 8 weeks compared to untreated controls at 12 weeks. The ligaments and inter-vertebral discs were surgically cut in all spines leaving the transverse process spinal fusion mass as the bridge between the vertebral bodies. Loading was applied until the fusion mass broke. The peak load was recorded for each sample. The data shown in FIG. 11 suggests that the 8 week treated group is at least as strong as the 12 week control with a trend towards greater bone strength.

Example 7—Analysis of Extracts of *Hibiscus tiliaceus* L

A method of investigating the composition of the extracts was developed using gas chromatographic-mass spectrometric (GC-MS) analysis. For example, GC-MS analysis was carried out on an extract of *Hibiscus tiliaceus* L. in coconut oil following extraction in ethanol and hydrocarbon (Example 2.3) and the hydrocarbon intermediate layer.

Figure 12A:
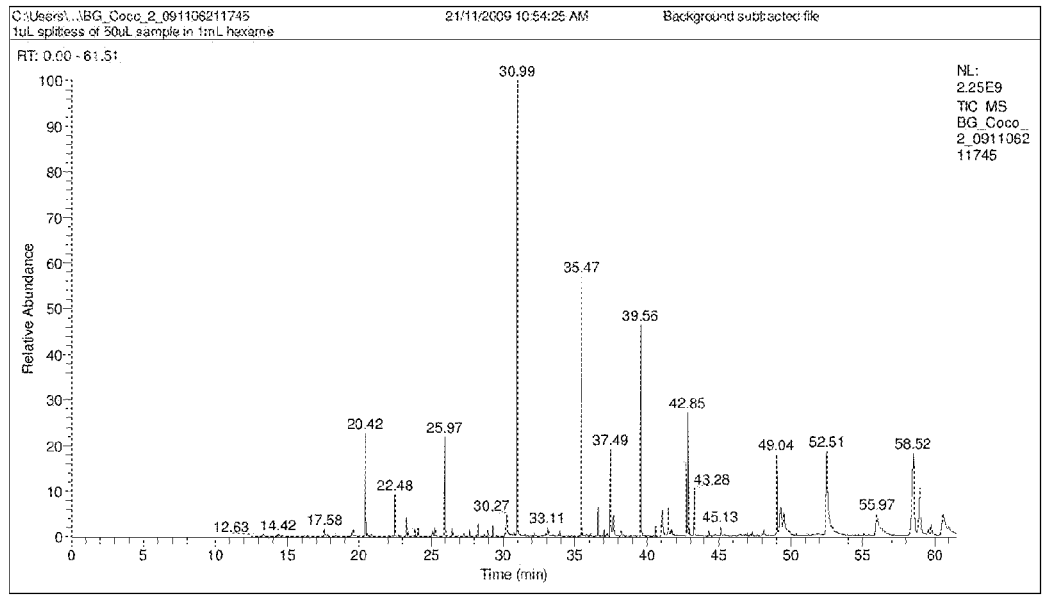
FIG. 12 show mass chromatograms of: A, *Hibiscus tiliaceus* L. in coconut oil following extraction in ethanol and hydrocarbon and; B, the hydrocarbon intermediate layer.
Figure 12B:
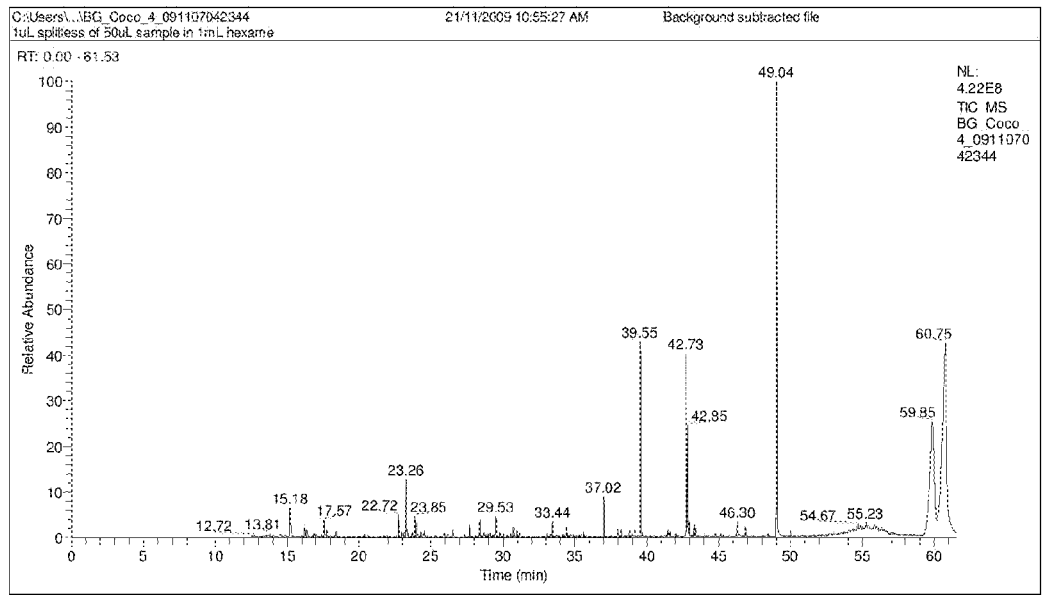

FIG. 12A shows mass chromatograms of an extract of *Hibiscus tiliaceus* L. in coconut oil with a main peak at 30.99 min. The intermediate layer also contained a peak at 30.99 min (FIG. 12B), however, the peak was at least seven times less than that observed in the extract of *Hibiscus tiliaceus* L. in coconut oil. In summary, the dominant peaks in the mass chromatograms of the extract of *Hibiscus tiliaceus* L. in coconut oil were at 30.99, 35.47, 37.48, 39.56, 42.85, 43.28, 49.04, 52.51, 55.97 and 58.54 min. The majority of the smaller peaks correspond to ethyl esters of fatty acids found in coconut oil.

The invention claimed is:

1. A method of bone or cartilage formation, repair or regeneration in a subject with a fracture, or a bone or cartilage injury in need thereof, comprising topically applying to skin of the subject surrounding the fracture or injury a composition comprising an effective amount of an extract of bark of *Hibiscus tiliaceus* obtained by extracting bark of *Hibiscus tiliaceus* with alcohol to form an alcohol extract and extracting the alcohol extract with coconut oil to provide the extract of bark of *Hibiscus tiliaceus*.

2. The method of claim 1, wherein the composition is applied prior to, during, or after a bone or cartilage graft or implantation procedure.

3. The method of claim 1, wherein the composition further comprises an effective amount of an extract of at least one plant material selected from the group consisting of leaves of *Vigna marina* (Burm.) Merr., husk of *Cocos nucifera* and leaves of *Terminalia catappa* L. obtained by extracting the at least one plant material in coconut oil.

4. The method of claim 1, wherein the composition enhances healing of an injury.

5. The method of claim 1, wherein the composition promotes bone or cartilage growth surrounding a bone or cartilage graft or implantable device.

6. The method of claim 5, wherein the graft is an autograft or allograft.

7. The method of claim 2, wherein the graft procedure is for repairing a bone fracture or for skeletal fusion.

8. The method of claim 1, wherein the composition is applied during an arthroscopic or open surgical procedure.

9. The method of claim 1, wherein the alcohol is ethanol.

10. A method of bone or cartilage formation, repair or regeneration in a subject with a fracture, or a bone or cartilage injury in need thereof, comprising topically applying to skin of the subject surrounding the fracture or injury a composition comprising an effective amount of a coconut oil extract of bark of *Hibiscus tiliaceus* obtained by extracting bark of *Hibiscus tiliaceus* with coconut oil to provide the coconut oil extract of bark of *Hibiscus tiliaceus*.

* * * * *